(12) United States Patent
Schmid

(10) Patent No.: US 10,151,481 B2
(45) Date of Patent: Dec. 11, 2018

(54) MATERIAL UTILIZATION WITH AN ELECTROPOSITIVE METAL

(75) Inventor: Günter Schmid, Hemhofen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1249 days.

(21) Appl. No.: 13/825,211

(22) PCT Filed: Sep. 16, 2011

(86) PCT No.: PCT/EP2011/066066
§ 371 (c)(1),
(2), (4) Date: Mar. 20, 2013

(87) PCT Pub. No.: WO2012/038329
PCT Pub. Date: Mar. 29, 2012

(65) Prior Publication Data
US 2013/0196271 A1    Aug. 1, 2013

(30) Foreign Application Priority Data

Sep. 20, 2010  (DE) .................. 10 2010 041 033

(51) Int. Cl.
*F23J 7/00*     (2006.01)
*B01D 53/62*    (2006.01)
(Continued)

(52) U.S. Cl.
CPC .............. *F23J 7/00* (2013.01); *B01D 53/62* (2013.01); *C01B 21/061* (2013.01); *C01C 1/026* (2013.01);
(Continued)

(58) Field of Classification Search
CPC ..................................... F23G 7/06; F23J 7/00
(Continued)

(56) References Cited

U.S. PATENT DOCUMENTS 2,138,122 A    11/1938  Roberts
3,101,592 A    8/1963   Robertson et al.
(Continued)

FOREIGN PATENT DOCUMENTS

CN    101618292 A    1/2010  ............ B01D 53/34
DE    2236208        2/1973
(Continued)

OTHER PUBLICATIONS

Der-Yan Hwang, Reaction mechanism of CO2 with Ca atom: A theoretical study, Dec. 8, 2000, Chemical Physics Letters, vol. 331, issues 5-6, pp. 526-532. https://www.sciencedirect.com/science/article/pii/S000926140001188X.*
(Continued)

*Primary Examiner* — Avinash Savani
*Assistant Examiner* — Aaron Heyamoto
(74) *Attorney, Agent, or Firm* — Slayden Grubert Beard PLLC

(57) ABSTRACT

A material is utilized with an electropositive metal. This can be used as post-oxyfuel process for oxyfuel power stations. Here, an energy circuit is realized by the material utilization. An electropositive metal, in particular lithium, serves as energy store and as central reaction product for the conversion of nitrogen and carbon dioxide into ammonia and methanol. The power station thus operates without $CO_2$ emissions.

11 Claims, 1 Drawing Sheet

(51) Int. Cl.

| | | |
|---|---|---|
| *C01B 21/06* | (2006.01) | |
| *C01C 1/02* | (2006.01) | |
| *C07C 29/151* | (2006.01) | |
| *F23B 99/00* | (2006.01) | |
| *F23G 7/06* | (2006.01) | |
| *F25J 3/04* | (2006.01) | |
| *C07C 1/02* | (2006.01) | |
| *F23J 15/00* | (2006.01) | |
| *F23L 7/00* | (2006.01) | |
| *B01D 53/14* | (2006.01) | |

(52) U.S. Cl.
CPC ............ *C07C 1/02* (2013.01); *C07C 29/1518* (2013.01); *F23B 99/00* (2013.01); *F23G 7/06* (2013.01); *F23J 15/00* (2013.01); *F23L 7/00* (2013.01); *F25J 3/04533* (2013.01); *F25J 3/04563* (2013.01); *B01D 53/1475* (2013.01); *B01D 2251/302* (2013.01); *B01D 2252/20484* (2013.01); *B01D 2256/20* (2013.01); *B01D 2257/504* (2013.01); *B01D 2258/0283* (2013.01); *C21C 2100/02* (2013.01); *C21C 2100/06* (2013.01); *F23B 2900/00003* (2013.01); *F23J 2215/10* (2013.01); *F23J 2215/50* (2013.01); *Y02C 10/04* (2013.01); *Y02E 20/12* (2013.01); *Y02E 20/326* (2013.01); *Y02E 20/344* (2013.01); *Y02P 10/132* (2015.11); *Y02P 10/212* (2015.11); *Y02P 10/34* (2015.11); *Y02P 20/152* (2015.11); *Y02W 30/54* (2015.05)

(58) Field of Classification Search
USPC .............................................. 431/4; 110/342
See application file for complete search history.

(56) References Cited

U.S. PATENT DOCUMENTS

| | | | |
|---|---|---|---|
| 3,759,036 A | 9/1973 | White | |
| 3,857,920 A | 12/1974 | Grantham et al. | |
| 4,698,974 A | 10/1987 | Wood | |
| 5,232,793 A | 8/1993 | Miyauchi et al. | |
| 6,206,685 B1 * | 3/2001 | Zamansky | B01D 53/56 110/210 |
| 6,370,865 B1 | 4/2002 | Sasaki et al. | |
| 7,739,968 B2 | 6/2010 | Borissov et al. | |
| 8,529,856 B2 * | 9/2013 | Smith | B01D 53/62 423/224 |
| 2002/0037810 A1 | 3/2002 | Nakagawa et al. | |
| 2008/0111104 A1 | 5/2008 | Lefenfeld et al. | |
| 2009/0238731 A1 * | 9/2009 | Liu | B01D 53/1475 422/178 |
| 2010/0261125 A1 * | 10/2010 | Olah | C01B 3/38 431/2 |
| 2011/0113844 A1 | 5/2011 | Schmid | |
| 2013/0260263 A1 | 10/2013 | Schmid | |

FOREIGN PATENT DOCUMENTS

| | | | | |
|---|---|---|---|---|
| DE | 3615027 | | 11/1987 | |
| DE | 4334257 | | 4/1995 | |
| DE | 4446964 | | 6/1995 | |
| DE | 69907843 | | 5/2004 | |
| DE | 102008031437 | | 1/2010 | |
| DE | 102009014026 | | 6/2010 | |
| DE | 102009014026 A1 * | 6/2010 | ............. F23B 90/00 |
| DE | 102010041033 | | 9/2010 | |
| EP | 0189659 | | 8/1986 | |
| EP | 0418864 | | 3/1991 | |
| EP | 2040323 | | 3/2009 | |
| WO | PCT/EP2011/066066 | | 9/2011 | |

OTHER PUBLICATIONS

Robert Rhein, Lithium Combustion: A Review, Dec. 1990, US Gov't, pp. 32 & 33.*
European Office Action, Application No. 15001258.1, 5 pages, dated Apr. 4, 2017.
Chinese Office Action for related Chinese Patent Application No. 201180055778.7, dated Dec. 2, 2014, 9 pages (including partial German translation).
International Search Report for PCT/EP2011/066066, dated Mar. 6, 2013.
Der-Yan Hwang et al., "Reaction Mechanism of $CO_2$ with Ca atom: A Theoretical Study," Chemical Physics Letters 331, 2000, 7 pages.
F. Ausfelder et al., "Verwertung and Speicherung von $CO_2$," Diskussionspapier, Dechema, Oct. 2008, 36 pages, http://www.dechema.de/dechema_media/diskussionco2.pdf.
European Search Report for related European Patent Application No. 14003134.5, dated Jan. 26, 2015, 9 pages.
F. W. Dafert et al., "Über einige neue Verbindungen von Stickstoff and Wasserstoff mit Lithium," Monatshefte für Chemie: An International Journal of Chemistry, Springer Wien, vol. 31, pp. 981-996 plus Abstract, 1910.

* cited by examiner

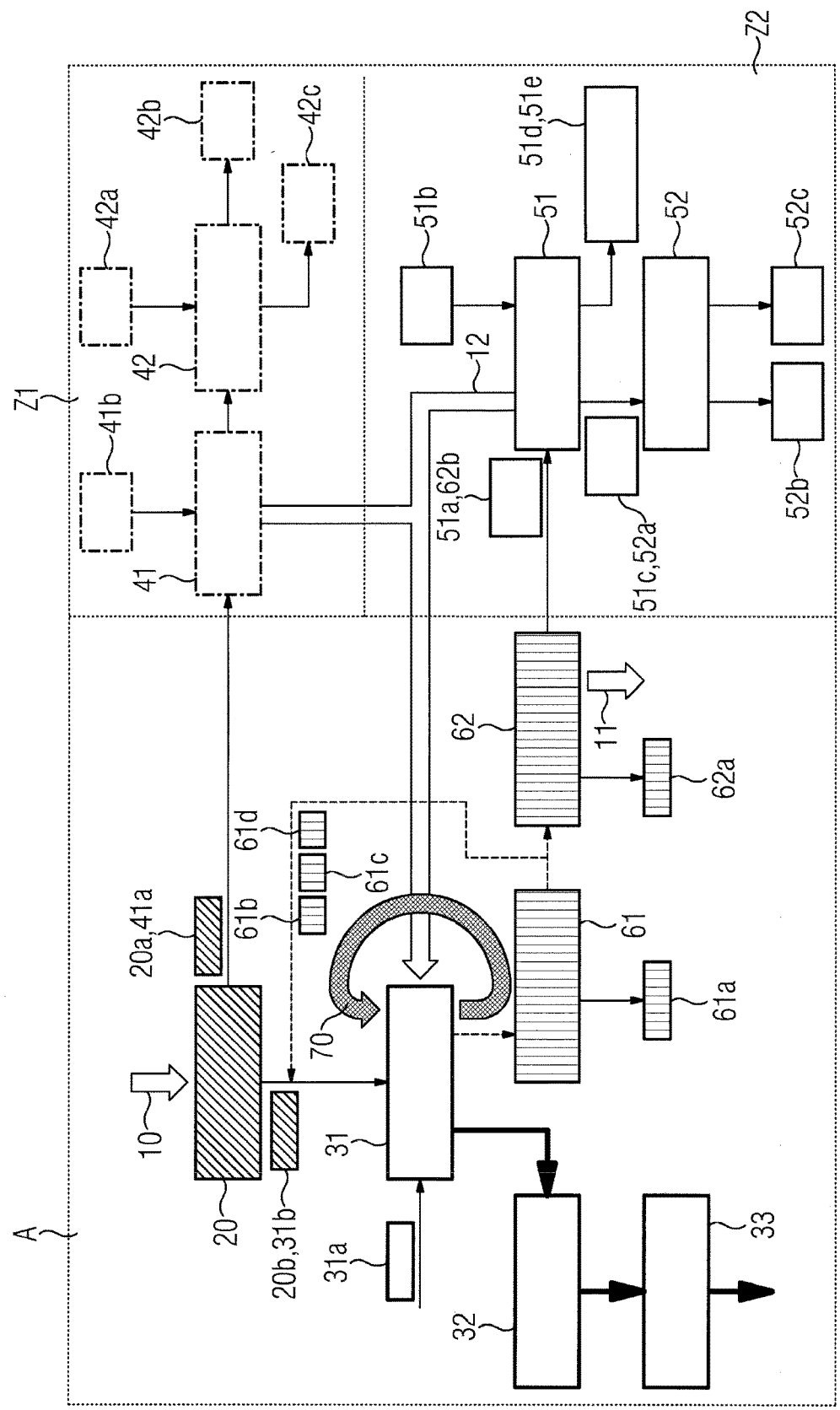

MATERIAL UTILIZATION WITH AN ELECTROPOSITIVE METAL

CROSS REFERENCE TO RELATED APPLICATIONS

This application is based on and hereby claims priority to International Application No. PCT/EP2011/066066 filed on Sep. 16, 2011 and German Application No. 10 2010 041 033.0 filed on Sep. 20, 2010, the contents of which are hereby incorporated by reference.

BACKGROUND

The present invention relates to the industrial utilization of materials.

In the field of power plant concepts, there is the known method in which coal is burned with pure oxygen and recirculated flue gas, in contrast to the conventional combustion of coal with air. For this purpose, before the combustion step, nitrogen and oxygen are separated from the air. Enrichment or upgrading of the $CO_2$ in the flue gas is thereby achieved. This process is found in the related art as an oxyfuel process. The $CO_2$ occurring during combustion can subsequently be captured in highly concentrated form. In corresponding known oxyfuel processes, the $CO_2$ occurs with such high density that it can subsequently be sequestered, that is to say, for example, stored in underground chambers. The oxyfuel process is often designated as being "emission-free". Emission-free in this context means simply that the $CO_2$ is not discharged into the atmosphere. It is stored, but not avoided.

SUMMARY

One possible object is to specify a method and an apparatus whereby materials, in particular waste products, can be utilized and further processed. In particular, the $CO_2$ emission is to be reduced and $CO_2$ sequestration is to be avoided.

The inventor proposes a method for industrial material utilization comprises a combustion step and a reaction step. In the reaction step, the conversion of at least one combustion product of the combustion step takes place. The combustion step comprises a reaction of an electropositive metal with the material to be utilized, in particular an exothermal reaction. In the reaction step, at least one combustion product of the combustion step is converted further. The reaction step may follow the combustion step directly. Alternatively, the combustion products may be captured and/or stored and/or transported before they are delivered to the reaction step. The combustion step and reaction step may therefore be independent of one another in terms of time and place.

By the method, for example, materials, such as nitrogen, carbon dioxide or else sulfur dioxide, are utilized. The material for utilization may be present in liquid or gaseous form. The method is expedient for the utilization of nitrogen or carbon dioxide or of gas mixtures which contain nitrogen and/or carbon dioxide, where appropriate still contaminated.

The method for material utilization, in particular the utilization of nitrogen and/or carbon dioxide, can be employed independently of a process for electrical energy generation. In particular, the method for utilizing nitrogen or carbon dioxide is adopted wherever nitrogen and carbon dioxide occur in a sufficiently high concentration, that is to say, in particular, also in sufficient purity. A carbon dioxide utilization process of this kind can be applied, for example, in the case of hitherto existing carbon dioxide stores or in any combustion of fossil fuels in which $CO_2$ of low entropy occurs. $CO_2$ of low entropy means that it is highly concentrated. Not just any combustion reaction with fossil fuels yields highly concentrated $CO_2$, for example not when combustion with air takes place, since in this case the $CO_2$ would be in a form diluted with the nitrogen of the air.

The method for material utilization may be combined with a method for the generation of electrical energy, in which the thermal energy generated in the combustion step and capable of being used in power plants is converted into electrical energy.

In an alternative method, for example, separation of oxygen and nitrogen from the air is carried out. Furthermore, for example, combustion of a fuel with the oxygen may be carried out. In this case, carbon dioxide of low entropy, that is to say highly concentrated carbon dioxide, occurs. The nitrogen which has been separated from the air and/or the carbon dioxide which has occurred are/is preferably delivered to the utilization method. This comprises the processing of the carbon dioxide and nitrogen or of only one of the two gases or its mixtures. Utilization takes place via a reaction with an electropositive metal. This affords the advantage that the $CO_2$ is processed virtually completely and only environmentally harmless or reutilizable end products remain. The method therefore has the advantage of generating electrical energy and of ensuring virtually complete utilization of secondary and waste products from, for example, electrical energy generation.

Carbon dioxide utilization offers the advantage that a $CO_2$ emission-free power plant can be implemented. For this purpose, the process of carbon dioxide utilization can follow the process for electrical energy generation by a power plant. The carbon dioxide which leaves the power plant may, for example, be converted into methanol by the $CO_2$ utilization process. The nitrogen utilization process may likewise follow a process for electrical energy generation, for example, by a power plant.

The nitrogen separated from the air is then further processed, for example according to the proposed method. In this case, for example, a reaction of the electropositive metal with the nitrogen is managed in the combustion step such that a nitride of the electropositive metal occurs, in the reaction step hydrolysis being carried out in which ammonia is produced from the nitride by the addition of water.

Alternatively, utilization of the nitrogen comprises a process step in which the nitrogen and water are converted directly into ammonia by the electropositive metal. In a further advantageous alternative, utilization of the nitrogen comprises a process step in which the nitrogen and water are directly converted sequentially into ammonia by the electropositive metal. In this case, therefore, for example, ammonia occurs as the end product. The generation of ammonia affords the advantage that other ammonia generation processes can consequently be replaced. Ammonia constitutes, in particular, one of the most important raw materials of the fertilizer industry. Ammonia has hitherto been produced by the Haber-Bosch process. The proposed method for the utilization of nitrogen therefore has the advantage of generating one of the most important initial materials which is necessary for the present-day energy and chemicals economy since this is based on fossil fuels. The nitrogen utilization process is preferably used as an ammonia synthesis process. By the nitrogen utilization process, nitrogen from the air can be bound and made available for the production of nutrients and biomass, without fossil fuels having to be provided for this purpose.

The oxyfuel process is an example of a process for the generation of electrical energy in which nitrogen and carbon dioxide are available in sufficient quantity, sufficient purity and suitable concentration. The utilization process preferably follows the oxyfuel process. The utilization process in the sense of a post-oxyfuel process affords an emission-free power plant concept.

In an advantageous refinement, the method is configured such that the processing of carbon dioxide comprises a combustion step and a synthesis step. In this case, once again, the combustion step comprises an exothermal reaction of the electropositive metal with the carbon dioxide. In this case, particularly during combustion, thermal energy is generated. The reaction is in this case preferably managed such that carbon monoxide occurs at the end. The synthesis step, in turn, preferably comprises the synthesis of methanol from the carbon monoxide and hydrogen. The chemical further processing of the combustion products thus preferably serves for the production of valuable basic chemicals.

In the combustion step of the electropositive metal with the carbon dioxide, oxides and carbonates of the electropositive metal occur as waste products. The carbon dioxide can be reduced to carbon by electropositive metals. However, the carbon formed in the combustion chamber may be comproportionated with further $CO_2$ to form carbon monoxide within the context of a Boudouard equilibrium, so that $CO_2$ is reduced to CO formally at the end by the electropositive metal.

The synthesis step comprises, for example, a reaction with hydrogen. CO and $H_2$ form, for example, a synthesis gas which may be used, inter alia, for methanol production. The advantage of this is that each carbon atom of the fossil energy carrier is used twice. In the first step, it is conventionally burnt to form $CO_2$, combustion being managed such that it occurs in highly concentrated form, for example in an oxyfuel process. In a second step, it can be reduced again by an electropositive metal and converted, for example, into a fuel for motor vehicles.

In a further advantageous refinement, the method comprises the processing of nitrogen, during which, in a combustion step, a nitride of the electropositive metal occurs as a result of an exothermal reaction of the electropositive metal with the nitrogen, and, in a hydrolysis step, ammonia is produced from the nitride by the addition of water. In particular, the processing of the nitrogen may also take place such that the nitrogen and water are converted directly into ammonia by the electropositive metal in a single process step. Alternatively, the processing of the nitrogen may also take place such that the nitrogen and water are converted into ammonia directly in succession by the electropositive metal in a single process step. A reaction step may comprise, for example, the addition of steam in the combustion step, so that ammonia occurs as a direct reaction. In this case, for example, the nitride is formed only intermediarily.

One advantage of nitrogen utilization is that ammonia is the end product. Ammonia is one of the most important initial materials for the fertilizer industry. Particularly in view of the future demand for biomass, an increased demand for fertilizer must also be expected. This demand can then be covered by the nitrogen utilization process, particularly in combination with a process for the generation of electrical energy, for example an oxyfuel process.

The utilization process may be employed as a post-oxyfuel process and can be applied to carbon dioxide and to nitrogen. Ammonia and methanol are advantageously generated. This is therefore chemical further processing of waste products which is used for the production of valuable further-utilizable basic chemicals.

In a further advantageous refinement, in the method heat transport is carried out, which delivers thermal energy, released particularly in the combustion step as a result of an exothermal reaction of the electropositive metal, to a step for the generation of electrical energy. Even the utilization process in itself generates in the combustion step energy in the form of high-temperature heat which can be used for generating electrical energy, for example via a steam turbine. The utilization process advantageously follows a process for the generation of electrical energy. The additional high-temperature heat occurring during the combustion of the electropositive metal with nitrogen or with carbon dioxide is additionally delivered for the generation of electrical energy.

In a further exemplary refinement, the method comprises a recovery process. In this recovery step, an oxide and/or a salt of the electropositive metal are/is converted into the metal again. Such reprocessing of the converted electropositive metal has the advantage that the overall circuit can be closed. Such reprocessing may be, for example, electrochemical reduction. In this case, in particular, oxides, hydroxides or salts of the electropositive metal can be converted into the metal again. In general, electrochemical reduction of the metal ion $M^{n+}$ can lead back to the metal M. For this purpose, once again, electrical energy is necessary which may be obtained, for example, from photovoltaic energy. In particular, such a process for the reprocessing or recovery of the electropositive metal may be considered as an energy store for energy obtained from photovoltaics. It is especially advantageous to carry out a recovery process for electropositive metals which are limited in terms of their occurrence in nature, such as, for example, lithium.

The proposed method and apparatus are expediently configured such that an electropositive metal with a normal potential lower than zero Volt is used. In the method, an electropositive metal of the first or the second main group is preferably used. In particular, lithium is used. Alternatively, electropositive metals, such as sodium, potassium, calcium, strontium, barium, magnesium or zinc, may also be employed. The natural resources of sodium and magnesium, for example, are not limited in terms of their occurrence. Although the quantity of lithium available worldwide is limited, a shortage is only to be expected in about 40 years. Here, once again, the recovery method has the advantage of making the process independent of the limited occurrence of lithium in nature.

Advantageously, for a method with a recovery process, photovoltaic energy is used for recovering the electropositive metal. Alternatively, any other form of regeneratively obtained electrical energy can also be employed for the electrochemical recovery process. The recovery process may take place separately in terms of time and space from the process for the generation of electrical energy, for example the oxyfuel process, and the utilization processes for nitrogen and carbon dioxide, for example in the form of a post-oxyfuel process.

According to the inventor's proposal, an apparatus which comprises a combustion chamber with an electropositive metal serves for material utilization. In this case, the combustion chamber serves for the combustion of the electropositive metal in the material. The combustion chamber is preferably configured such that the material, a gas or a liquid can be introduced into the combustion chamber, and such that a combustion step with an exothermal reaction of an electropositive metal can be carried out.

In an advantageous refinement, the apparatus for material utilization is arranged with a reaction chamber which serves for the further conversion of at least one combustion product. For this purpose, the reaction chamber is configured such that a combustion product can be introduced from the combustion chamber into the reaction chamber and conversion of the combustion product can be carried out. In this case, for example, ammonia is obtained from nitrogen utilization and, for example, methanol is obtained from carbon dioxide utilization.

In a further advantageous refinement, an arrangement comprises a utilization apparatus and, for example, an air separation plant. By the air separation plant, for example, oxygen and nitrogen are separated from the air.

In a further advantageous refinement, the utilization apparatus is expediently arranged with an apparatus which serves for the generation of electrical energy. This may be, for example, a power plant. In particular, a steam turbine is included.

The arrangement further comprises, for example, a combustion chamber which is configured for the combustion of a fuel with the oxygen. For example, the carbon dioxide which has occurred during combustion is discharged via a separation device. A separation device for discharging the separated nitrogen may also be included.

In a further advantageous refinement, the utilization apparatus is connected to the power plant such that the separated nitrogen can be introduced into the combustion chamber. For example, a second utilization apparatus is advantageously connected to the power plant such that the carbon dioxide discharged via the separation device can be introduced into the combustion chamber.

In current power plants, for example, a mixture of nitrogen and carbon dioxide occurs as waste. If this mixture is further processed with an electropositive metal, the reaction with carbon dioxide proceeds much more vigorously than with nitrogen. In particular, CO2 can thus be separated as lithium carbonate from the exhaust gas.

The advantage of nitrogen utilization and of carbon dioxide utilization is that, in the combustion step in the combustion chamber, energy is generated in the form of high-temperature heat which can be used for the generation of electrical energy. Preferably, an apparatus for nitrogen utilization or an apparatus for carbon dioxide utilization or in each case an apparatus for nitrogen utilization and in each case one for carbon dioxide utilization is coupled to a power plant. In this case, the energy generated in the combustion chamber in the combustion step can be additionally delivered in the form of high-temperature heat to the power plant, in particular the steam generator in the power plant, and can serve for the generation of electrical energy. Furthermore, carbon dioxide utilization affords the advantage that CO2 emission can be prevented or can be greatly reduced. The carbon dioxide which occurs during the combustion of fossil fuels can be converted virtually completely into a reutilizable end product by the apparatus. For example, methanol is generated. A further advantage of nitrogen utilization is that a waste product, such as, for example, ammonia, can be generated, this being one of the most important raw materials in the fertilizer industry. Overall, the advantage is that the exploitation chain for the power plant constructor and power plant operator is prolonged.

In an advantageous refinement, the arrangement comprises a utilization apparatus for carbon dioxide with a combustion chamber and a reaction chamber. In this case, the combustion chamber is preferably configured such that it is suitable for a combustion step with exothermal reaction of an electropositive metal with carbon dioxide. In particular, the combustion chamber is configured such that the reaction can be managed such that carbon monoxide occurs at the end. In principle, during the exothermal reaction of the electropositive metal with the carbon dioxide, carbon can also be generated. However, this can be comproportionated further to form carbon monoxide as a result of the Boudouard equilibrium. The reaction chamber is advantageously equipped with a synthesis gas reactor. In particular, the reaction chamber is coupled to a synthesis gas reactor which makes it possible to react hydrogen with the carbon monoxide. For example, the reaction chamber is followed by a synthesis gas reactor. The synthesis gas reactor, in turn, may be configured such that it is suitable for the synthesis of methanol from carbon monoxide and hydrogen. Such an apparatus for carbon dioxide processing can be mounted and operated, for example, wherever carbon dioxide occurs in a suitable form, that is to say has low entropy and is highly concentrated. In addition to power plants, therefore, already existing carbon dioxide storage reservoirs may also be envisaged as a source for carbon dioxide utilization.

In a further expedient refinement, a utilization apparatus for nitrogen is configured with a combustion chamber and with a reaction chamber. The combustion chamber is configured, for example, for a combustion step with an exothermal reaction of an electropositive metal with the nitrogen. During such a combustion reaction, for example, a nitride of the electropositive metal may arise or occur as an intermediate. Furthermore, the reaction chamber is configured such that, in it, ammonia can be produced from the nitride of the electropositive metal by hydrolysis with the addition of water. Alternatively, a hydrolysis chamber is mounted next to the reaction chamber.

For example, the proposals are configured such that the apparatus for the generation of ammonia from nitrogen provides a utilization apparatus which is configured with only one combined combustion and reaction chamber. Process management is expediently possible in this combined combustion and reaction chamber, so that nitrogen and water can be converted directly into ammonia by the electropositive metal.

For example, lithium may be used as an electropositive metal for the conversion or utilization of nitrogen. In the combustion of lithium in nitrogen, a value for energy release of 16

$$\frac{\text{kcal}}{\text{mol} \cdot \text{electron}}$$

is obtained. This notation is therefore standardized to the number of electrons converted in the reaction. During the combustion of carbon in oxygen, a value for energy release of 24

$$\frac{\text{kcal}}{\text{mol} \cdot \text{electron}}$$

is obtained, which is therefore only slightly higher than that for the combustion of lithium in nitrogen. This shows the first advantage of the process of nitrogen utilization, to be precise that, in turn, energy can be generated in the form of high-temperature heat which can be used for the generation of electrical energy. However, the lithium nitride occurring during this combustion reaction does not have to be a waste product, the lithium nitride can be converted further. Lithium nitride reacts, for example, exothermally with water to form ammonia. A further end product of this reaction is lithium hydroxide which can be reduced to lithium again in a recovery reaction.

Ammonia has hitherto been produced by fossil fuels. The nitrogen utilization method is an alternative ammonia production method. Three percent of the world's total expenditure of fossil energy is consumed for the purpose of the production of ammonia. This shows the major advantage of nitrogen utilization.

The reaction does not always have to be managed sequentially. For example, process management in the combustion chamber may be configured such that nitrogen and water can be converted directly into ammonia by lithium. The binding of the oxygen contained in the water molecule can take place by lithium being converted into lithium oxide, thus making it possible, overall, to increase the heat tone of the reaction.

Furthermore, lithium nitride can also react as a superbase with molecular hydrogen to form lithium amide and lithium hydride. Lithium hydride is a potential high-temperature hydrogen store which at 270° C. gives off its hydrogen reversibly again.

Advantageously, the utilization apparatus is arranged with a power plant (A) for the generation of electrical energy. A steam turbine is advantageously included for the purpose of generating electrical energy from the thermal energy of the combustion of the electropositive metal. A steam turbine may also be included in each case in the utilization apparatus or in the power plant. An arrangement composed of a power plant and of two utilization apparatuses for nitrogen and carbon dioxide may comprise up to three steam generators.

In a further advantageous refinement, the arrangement comprises a heat transport device which connects the power plant to the combustion chamber of one of the utilization apparatuses. In particular, a heat transport device may be included which connects the power plant to both combustion chambers of the utilization apparatuses for nitrogen and carbon dioxide. The heat transport device is configured such that thermal energy, released particularly as a result of a combustion step in one of the combustion chambers, can be transported and made available to the power plant. In particular, heat can be transported to a combustion chamber in the power plant. For example, additional high-temperature heat is delivered to the steam generator in the power plant from the combustion chambers of the utilization apparatuses for the nitrogen and carbon dioxide for the generation of electrical energy. This refinement has the advantage of a twofold use of nitrogen and carbon dioxide as the original waste products. Not only is CO2 emission thereby greatly reduced, but, as a result of the combustion process, additional high-temperature heat is made available for the generation of electrical energy. Furthermore, the apparatus for carbon dioxide utilization has the advantage, in particular, of making methanol available as an exit product. The apparatus for nitrogen utilization likewise offers the advantage of making additional high-temperature heat available from the combustion reaction, in addition to ammonia as an important exit product.

The central element for nitrogen and carbon dioxide utilization is an electropositive metal, in particular lithium. This is not consumed itself during the process, but instead changes only the oxidation stage. The circuit can thus be closed by a recovery process. In particular, solar energy is used for the recovery process. Electropositive metals which are suitable for the post-oxyfuel process thus also form solar energy stores.

New possibilities for storage will be of great interest in the future particularly for markets where regenerative energies are generated without any inherent possibility for storage, such as, for example, energy from the sun, wind, tides or biomass. In this case, the recovery, that is to say recycling, of the electropositive metals used in the post-oxyfuel process can be adopted. This also would not give rise to competition in the transport of electrical energy over long distances by cable. For example, at the present time, coal or petroleum, as energy carriers, are also transported out of the producer countries, instead of being converted into current on the spot in the producer countries. With electropositive metals as energy stores, for example for solar energy, the existing energy generation landscape can be made more climatically and environmentally friendly, but also, in the long term, in electropositive metals as energy stores, the potential can be seen that fossil energy carriers can be superseded completely. In this respect, combustion of the electropositive metals in air could also be conceivable.

BRIEF DESCRIPTION OF THE DRAWINGS

These and other objects and advantages of the present invention will become more apparent and more readily appreciated from the following description of the preferred embodiments, taken in conjunction with the accompanying drawings of which:

The FIGURE shows a flowchart which depicts the entire process flow and illustrates diagrammatically the apparatuses necessary for a power plant. The central process steps are illustrated by large boxes or rectangles, small boxes illustrating the entry and exit products of the process steps. With reference to a power plant, the boxes may also stand by way of example for various apparatuses and chambers. The arrows between the boxes indicate the process flow, in particular the chronological process flow. With reference to entry and exit products of the various process steps, the arrows also indicate the introduction and discharge of the products. Simple arrows stand for the introduction, discharge and transfer of products or of the material. The thick arrows illustrated as being hollow stand for energy entry, exit or transport.

DETAILED DESCRIPTION OF THE PREFERRED EMBODIMENT

Reference will now be made in detail to the preferred embodiments of the present invention, examples of which are illustrated in the accompanying drawings, wherein like reference numerals refer to like elements throughout.

A standard oxyfuel power plant A is illustrated diagrammatically on the left side of the FIGURE. The following process steps or apparatuses are depicted from the top downward: the air separation plant 20 requires a certain energy introduction 10 for the separation of air. Nitrogen 20*a* emerges from the air separation plant to one side. Furthermore, oxygen 20*b* emerges. The nitrogen 20*a* is processed further in the first further-processing apparatus Z1. For this purpose, it is discharged from the power plant A, from the air separation plant 20 and constitutes a first entry product 41*a* for the further-utilization apparatus Z1. The oxygen 20*b* which emerges from the air separation plant 20 is introduced as an entry product 31*b* into the steam generator 31. Furthermore, coal or, in general, a fossil fuel 31*a* is introduced into the steam generator 31, as well as further oxygen 61*b*, carbon dioxide 61*c* and water 61*d* which is introduced into the steam generator 31 again by a flue gas recirculation process 70. The combustion of the fossil fuel 31a, in particular of coal, under an oxygen atmosphere takes place in the steam generator 31. By heat energy thereby generated, a steam turbine 32 is driven and, in turn via the latter, a generator 33 is driven, by which electrical energy can be generated. Alternatively, it is possible to conduct the hot combustion gases directly to a gas turbine.

After combustion in the steam generator 31, the combustion products first enter the dust separation apparatus 61. Dust 61a is discharged from the power plant via this dust separation device 61. Furthermore, carbon dioxide 61c, oxygen 61b and, in parts, water 61d are recirculated, that is to say recirculated into the combustion chamber of the steam generator 31. The not yet consumed oxygen 61b is thus used once more for combustion and ensures that highly concentrated carbon dioxide is available as exit product at the end and is no longer recirculated to the steam generator. Water 62a and highly concentrated carbon dioxide 62b are discharged as exit products via the flue gas purification apparatus 62. Furthermore, low-temperature heat 11 is discharged by the flue gas purification apparatus 62. Dust separation 61 and flue gas purification 62 together form the separation device. Carbon dioxide 62b as the exit product from the separation device is introduced for further processing into the second utilization apparatus for carbon dioxide Z2. Carbon dioxide 51a forms there a first entry product into the combustion chamber 51 of the further-processing device Z2.

The further-processing devices Z1/Z2 are mounted directly on the oxyfuel power plant A so that nitrogen 20a/41a and carbon dioxide 51a/62b can be discharged directly from the power plant and introduced into the further-processing devices Z1/Z2. More specifically, the nitrogen 20a/41a and carbon dioxide 51a/62b are introduced directly into the respective combustion chambers 41/51 of the further-processing devices Z1/Z2.

The carbon dioxide 41a is combusted together with lithium 41b in the combustion chamber 41. In this case, high-temperature heat 12 occurs which, in addition to the heat which has occurred, can be recirculated and used in the power plant for steam generation 31. The exit product of the combustion chamber 41 is lithium nitride which is transferred into the hydrolysis chamber 42. The lithium nitride which has occurred is in no way a waste product. It reacts exothermally with water to form ammonia 42b. Ammonia is one of the most important exit products in fertilizer production. In the current related art, ammonia is produced by fossil fuels. In this case, 3% of the world's total expenditure of fossil energy is taken up by the production of ammonia. To be precise, without fertilizer, the economical production of biomass is impossible.

For example, the combustion chamber is configured such that $Li_3N$ is generated in the upper or front part. The dust then flies at high velocity along a pipe. Steam is then introduced in the lower or rear part of the combustion chamber. At the end, a gas/dust mixture of $Li_2O$, ammonia and excess $H_2O$ is obtained.

If combustion is standardized to the number of electrons converted, the combustion of carbon in oxygen yields an energy release of 24

$$\frac{kcal}{mol \cdot electron}.$$

The combustion of lithium in nitrogen yields an energy release of 16

$$\frac{kcal}{mol \cdot electron}.$$

This value is only about 30% lower, thus making it possible to use lithium combustion in nitrogen compatibly with power plants and on an industrial scale.

Ammonia 42b and lithium hydroxide 42c emerge as exit products from the hydrolysis chamber 42. The lithium hydroxide can be recirculated into lithium by electrochemical reduction. A requisite entry product for the hydrolysis step is water 42a. Correspondingly to the further processing of nitrogen, carbon dioxide 62b/51a is also introduced for further processing into the combustion chamber 51 of the further-processing device or utilization apparatus Z2. Furthermore, lithium 51b is introduced into the combustion chamber 51. The lithium 51b is combusted under a carbon dioxide atmosphere. In this case, high-temperature heat 12 again occurs which can be delivered to the power plant, in particular to the steam generation process 31. The reaction of lithium with CO2 is highly exothermal. Carbon monoxide 51c, lithium oxide and lithium carbonate 51d/e occur as exit products of the combustion reaction 51. The lithium oxide and lithium carbonate can be reduced electrochemically and thus recirculated into lithium. This takes place for example via intermediate steps, such as, for example, chloride. The carbon monoxide 51c constitutes at the same time the entry product 52a for the following synthesis step. It is introduced into the synthesis gas reactor 52. For this purpose, a further entry product is hydrogen 52d. Together with the carbon monoxide 52a and with the hydrogen 52d, synthesis gas is thus obtained which can be used, inter alia, for methanol production. Methanol 52c is therefore one of the exit products of the synthesis gas reactor 52 or synthesis step.

An oxyfuel power plant A is a modern plant for generation of electrical energy. In this case, carbon dioxide occurs in a highly concentrated form. Moreover, relatively pure nitrogen occurs. If these gases are used further, the effectiveness of the overall system increases. The process chain is prolonged by the reduction of carbon dioxide and nitrogen. Restructuring of the fertilizer market can take place via the exit products, for example, ammonia. Methanol as an exit product is important for fuel production, since it is no longer generated from fossil raw materials as energy carriers, but instead in an environmentally and climatically friendly way by lithium as solar energy store. Lithium is therefore designated as solar energy store since it can be obtained from its oxides or salts by photovoltaically generated electrical energy.

The fossil energy carrier market can thus give volume to the growing alkali metal or lithium market. To generate the same quantity of thermal energy, a power plant requires fewer fossil fuels. The carbon atoms required for the production of fuels come from carbon dioxide of low entropy, that is to say highly concentrated carbon dioxide. During combustion in a motor vehicle, it becomes carbon dioxide of high entropy and can then be recycled only by plants. The fuel market is carbon dioxide-neutral comparably to fuels from biomass. The alkali metal or lithium market will consequently grow sharply. At the same time, markets in the development of a lithium infrastructure will arise. On the one hand, this involves the generation of lithium and, on the other hand, its recycling.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

The invention claimed is:

1. A method for industrial utilization of carbon dioxide, comprising:
   receiving highly concentrated carbon dioxide produced by a fuel combustion process in which a fossil fuel is combusted with oxygen to produce the highly concentrated carbon dioxide and to generate electrical energy; and
   converting the carbon dioxide produced by the fuel combustion process to methanol by:
      in a lithium combustion process after the fuel combustion process, reacting the carbon dioxide with lithium to produce at least carbon monoxide and lithium carbonate as combustion products; and
      in a reaction process, adding hydrogen to the carbon monoxide to produce methanol, such that carbon atoms of the fossil fuel are (a) burnt to form highly concentrated carbon dioxide and (b) reduced by the lithium and converted to methanol.

2. The method as claimed in claim 1, wherein in the lithium combustion process, thermal energy is generated, and the method further comprises converting the thermal energy into electrical energy.

3. The method as claimed in claim 1, comprising reacting nitrogen with lithium to produce a nitride of the electropositive metal, wherein the nitrogen-lithium reaction process comprises hydrolysis of the nitride to add water and produce ammonia.

4. The method as claimed in claim 3, wherein the lithium combustion process and nitrogen-lithium reaction process are combined into one process in which nitrogen and water are converted directly into ammonia by the electropositive metal.

5. The method as claimed in claim 3, wherein before the combustion process, nitrogen is separated from air and the nitrogen is delivered to the nitrogen-lithium combustion process.

6. The method as claimed in claim 1, wherein the method further comprises a recovery process, in which the lithium carbonate is converted back to lithium.

7. The method as claimed in claim 1, further comprising electrochemically reducing the lithium carbonate produced in the second combustion process to thereby recirculate the lithium carbonate into lithium.

8. A method for industrial utilization of carbon dioxide, comprising:
   in a first combustion process, combusting a fossil fuel with oxygen to produce highly concentrated carbon dioxide and to generate electrical energy,
   delivering the carbon dioxide produced by the first combustion process to a second combustion process;
   in the second combustion process, reacting the carbon dioxide with lithium to produce at least carbon monoxide and lithium carbonate as combustion products; and
   in a reaction process, adding hydrogen to the carbon monoxide to produce methanol,
   such that carbon atoms of the fossil fuel are (a) burnt to form highly concentrated carbon dioxide and (b) reduced by the lithium and converted to methanol; and
   electrochemically reducing the lithium carbonate produced in the second combustion process to thereby recirculate the lithium carbonate into lithium.

9. The method of claim 8, wherein the second combustion produces carbon monoxide, lithium oxide, and lithium carbonate; and
   the method further comprises electrochemically reducing the lithium oxide to thereby recirculate the lithium oxide into lithium.

10. The method as claimed in claim 8, wherein thermal energy is generated in the lithium combustion process, and the method further comprises converting the thermal energy into electrical energy.

11. The method as claimed in claim 8, further comprising reacting nitrogen with lithium to produce a nitride of the electropositive metal, wherein the nitrogen-lithium reaction process comprises hydrolysis of the nitride to add water and produce ammonia.

* * * * *